United States Patent
Fuller et al.

(10) Patent No.: US 10,875,847 B2
(45) Date of Patent: Dec. 29, 2020

(54) AMINOPYRAZOLES AS SELECTIVE JANUS KINASE INHIBITORS

(71) Applicant: Intervet Inc., Madison, NJ (US)

(72) Inventors: Peter H. Fuller, Ashland, MA (US); Jason Brubaker, Cambridge, MA (US); Jonathan R. Young, Poway, CA (US)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 16/468,548

(22) PCT Filed: Dec. 13, 2017

(86) PCT No.: PCT/EP2017/082529
§ 371 (c)(1),
(2) Date: Jun. 11, 2019

(87) PCT Pub. No.: WO2018/108969
PCT Pub. Date: Jun. 21, 2018

(65) Prior Publication Data
US 2020/0115367 A1    Apr. 16, 2020

Related U.S. Application Data

(60) Provisional application No. 62/434,154, filed on Dec. 14, 2016.

(51) Int. Cl.
*C07D 405/14* (2006.01)
*A61P 17/04* (2006.01)

(52) U.S. Cl.
CPC ............ *C07D 405/14* (2013.01); *A61P 17/04* (2018.01)

(58) Field of Classification Search
None
See application file for complete search history.

(56) References Cited

U.S. PATENT DOCUMENTS

| | | |
|---|---|---|
| 6,890,929 B2 | 5/2005 | Blumenkopf et al. |
| 7,687,507 B2 | 3/2010 | Blumenkopf et al. |
| 8,133,899 B2 | 3/2012 | Mitton-fry et al. |
| 8,987,283 B2 | 3/2015 | Mitton-fry et al. |

FOREIGN PATENT DOCUMENTS

| | | |
|---|---|---|
| WO | 2013040863 A1 | 3/2013 |
| WO | WO2013041042 A1 | 3/2013 |
| WO | 2014146490 A1 | 9/2014 |

OTHER PUBLICATIONS

Siu T et al, The discovery of 3-((4-chloro-3-methoxyphenyl)amino)-1-((3R,4S)-4-cyanotetrahydro-2H-pyran-3-yl)-1H-pyrazole-4-carboxamide, a highly ligand efficient and efficacious janus kinase 1 selective inhibitor with favorable pharmacokinetic properties, Journal of Medicinal Chemistry, 2017, pp. 9676-9690, vol. 60, No. 23.
Carmi-Levy, IRIT, A Modular View of Cytokine Networks in Atopic Dermatitis, Clinic Rev. Allerg. Immunol., 2011, 245-253, 41.
Cosgrove, Sallie B., A blinded, randomized, placebo-controlled trial of the efficacy and safety of the Janus kinase inhibitor oclacitinib (Apoquel) in client-owned dogs with atopic dermatitis, Veterinary Dermatology, 2013, 587-e142, 24.
Cosgrove, Sallie B., Efficacy and safety of oclacitinib for the control of pruritus and associated skin lesions in dogs with canine allergic dermatitis, Veterinary Dermatology, 2013, 479-e114, 24.
Dillon, Stacey R., Interleukin 31, a cytokine produced by activated T cells, induces dermatitis in mice, Nature Immunology, 2004, 752-760, 5(7).
European Medicines Agency, Science Medicines Health, CVMP assessment report for APOQUEL (EMEA/V/C/002688/0000) International non-proprietary name: oclacitinib maleate, Veterinary Medicines and Product Data Management, 2013, 1-20, EMA/481054/2013.
Ghoreschi, Kamran, Janus kinases in immune cell signaling, Immunological Reviews, 2009, 273-287, 228.
Gonzales, A.J. Oclacitinib (APOQUEL) is a novel Janus kinase inhibitor with activity against cytokines involved in allergy, Journal of Veterinary Pharmacology and Therapeutics, 2014, 317-324, 37.
Hill, P.B., Development of an owner-assessed scale to measure the severity of pruritus in dogs, Veterinary Dermatology, 2007, 301-308, 18.
Minegishi, Yoshiyuki, Human Tyrosine Kinase 2 Deficiency Reveals Its Requisite Roles in Multiple Cytokine Signals Involved in Innate and Acquired Immunity, Immunity, 2006, 745-755, 25.
O'Shea, John J., A New Modality for Immunosuppression: Targeting the JAK/STAT Pathway, Nature Reviews Drug Discovery, 2004, 555-564, 3.
Olivry, Thierry, Validation of the Canine Atopic Dermatitis Extent and Severity Index (CADESI)-4, a simplified severity scale for assessing skin lesions of atopic dermatitis in dogs, Veterinary Dermatology, 2014, 77-e25, 25.
Ong, Peck Y., Immune Dysregulation in Atopic Dermatitis, Current Allergy and Asthma Reports, 2006, 384-389, 6(5).
Yamaoka, Kunihiro, Protein family review the Janus kinases (Jaks), Genome Biology, 2004, 253-258, 5(12).
Zoetis Inc., APOQUEL, Oclacitinib Tablet, Dogs, Freedom of Information Summary, 2013, 1-28, NADA 141-345.

*Primary Examiner* — Kamal A Saeed
(74) *Attorney, Agent, or Firm* — David J. Kerwick

(57) ABSTRACT

The instant invention provides compounds of formula I which are selective JAK inhibitors, and as such are useful for the treatment of JAK-mediated diseases such as atopic dermatitis, arthritis, and cancer.

18 Claims, 1 Drawing Sheet

Values with different letters are significantly different (p<0.05; Tukey's multiple comparison test)

AMINOPYRAZOLES AS SELECTIVE JANUS KINASE INHIBITORS

CROSS-REFERENCE TO RELATED APPLICATIONS

This application is a national stage entry under 35 U.S.C. § 371 of PCT/EP2017/082529, filed on Dec. 13, 2017, which claims priority to U.S. Provisional Application No. 62/434,154, filed on Dec. 14, 2016; the content of PCT/EP2017/082529 is hereby incorporated by reference in its entirety.

BACKGROUND OF THE INVENTION

Protein kinases are a group of enzymes that regulate the activity of their target proteins by the addition of phosphate groups to the protein substrate. Kinases can be subdivided by their target into Serine/Threonine kinases and Tyrosine kinases, and play an essential role in many physiological processes including cell division, differentiation, cellular homeostasis and signal transduction.

The mammalian Janus kinase (JAK) family of non-receptor tyrosine kinases has four members; JAK1, JAK2, JAK3 and TYK2. The JAK family is involved in intracellular signal transduction from >70 different cytokines. Cytokines bind to their cell surface receptors resulting in receptor dimerization and subsequent activation/phosphorylation of JAK tyrosine kinases. Specific tyrosine residues on the receptor are then phosphorylated by activated JAKs and serve as docking sites for STAT proteins. STATs are phosphorylated by JAKs, dimerize, then translocate to the nucleus where they bind specific DNA elements and activate gene transcription. JAK1 signals in conjunction with all JAK isoforms in a cytokine dependent manner.

JAKs are essential for multiple physiological functions. This is evidenced by studies using genetically engineered mouse models that are deficient in specific JAKs (K. Ghoreschi, A. Laurence, J. J. O'Shea, Immunol. Rev. 228, 273 (2009)), and the identification of mutations in the JAK enzymes that have been associated with diseases in humans. (J. J. O'Shea, M. Pesu, D. C. Borie, P. S. Changelian, Nat. Rev. Drug Discov. 3, 555 (2004)). (Y. Minegishi et al., Immunity. 25, 745 (2006)).

These mouse and human genetic data link the Jak/STAT pathway to various diseases and disorders including but not limited to hyperproliferative disorders and cancer such as leukemia and lymphomas, immunological and inflammatory disorders such as transplant rejection, asthma, chronic obstructive pulmonary disease, allergies, rheumatoid arthritis, allergic and atopic dermatitis, type I diabetes, amyotropic lateral sclerosis and multiple sclerosis.

WO 2013/041042 discloses pyrazole carboxamdines as Janues Kinase Inhbitors that are useful for the treatment of rheumatoid arthritis, asthma, COPD and cancer. The compounds of this disclosure are of the following formula

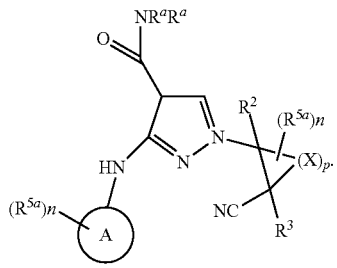

WO2013/040863 discloses substituted cycloalkylnitrile pyrazole carboxamides that are Janus kinase 1 inhibitors useful for treating e.g. asthma, obstructive airways diseases, arthritis, emphysema, cancer, myasthenia gravis, Graves disease, and Alzheimer's disease.

WO2014/146490 discloses substituted 2-(3-amino-4-oxo-4,5-dihydro-pyrazolo(4,3-c)pyridin-1-yl)-cyclobutanecarbonitrile compounds are Janus kinase inhibitors used to treat e.g. rheumatoid arthritis, chronic asthma, chronic obstructive pulmonary disease, diabetes.

Cytokines which utilize the JAK-STAT signaling pathway have been implicated in the pathogenesis and maintenance of atopic and allergic dermatitis. These include the pro-inflammatory IL-4 and IL-6, and IL-13 [Carmi-Levy et al., Clinic Rev Allerg Immunol (2011), 41:245), Ong and Leung, Curr. Allergy Asthma Rep. (2006), 6(5):384)], cytokines involved in the allergic response, as well as IL-31, a cytokine involved in eliciting pruritis [Dillon et al., Nat. Immunol. (2004), 5(7): 752]. Importantly, the receptors of these aforementioned cytokines involved in atopic and allergic dermatitis utilize JAK1, complexed with JAK2, JAK3, or Tyk2, to generate intracellular signaling and elicit biological effects [Yamaoka K, Saharinen P, Pesu M, Holt V E 3rd, Silvennoinen O, O'Shea J J., Genome Biol. 2004; 5(12):253].

In dogs with allergic or atopic dermatitis, the administration of oclacitinib, a JAK inhibitor with modest selectivity for JAK1, produces a rapid amelioration of pruritus and reduces lesions [Cosgrove et al., Vet. Derm. (2013), 24:479; Cosgrove et al., Vet. Derm. (2013), 24:587]. At higher doses, oclacitinib produces a reduction in hematocrit, hemoglobin, and reticulocyte counts, presumably due to inhibition of JAK2 [FOI Summary NADA 141-345; Gonzales et al., J. Vet. Pharmacol. Therapeut. (2014), 37:317]. Collectively, these data strongly suggest that inhibition of JAK1 is an effective treatment for allergic and atopic dermatitis in dogs, and that a compound with higher selectivity for JAK1 over the other JAK enzymes will confer an improved therapeutic index.

Apoquel® is an animal drug whose active ingredient is oclacitinib which is authorized for the control of pruritus associated with atopic dermatitis and control of atopic dermatitis in dogs at least 12 months in age (See FOI Summary for NADA 141-345, May 14, 2013). See also U.S. Pat. Nos. 6,890,929; 7,687,507; 8,133,899 and 8,987,283.

Apoquel® safety was evaluated in a pivotal 6 month, good laboratory practice (GLP) margin of safety study. The product was administered orally, twice per day for 6 weeks, followed by once per day for 20 weeks, to dogs at 1, 3, and 5 times the maximum exposure dose of 0.6 mg/kg (recommended clinical dose is 0.4 mg/kg) for a total of 26 weeks (6 months). Although the product was generally well tolerated at all doses, there were test article effects in all groups consistent with the pharmacological action of the drug class. These included: papillomas (considered test article related, but not dose related); interdigital cysts (pododermatitis, etc) (probably dose-related); decreases in red cell mass; decreases in serum albumin; decreased cellularity of gut-associated lymphoid tissue (GALT), spleen, and cervical/mesenteric lymph nodes; decreased cellularity of sternal and femoral bone marrow. Most of these effects were mild and appeared non-progressive (see CVMP assessment report for APOQUEL (EMEA/V/C/002688/0000); EMA/481054/2013).

SUMMARY OF THE INVENTION

The present invention provides novel compounds which are inhibitors of JAKs. The invention also provides a method for the treatment and prevention of JAK-mediated diseases and disorders using the novel compounds, as well as pharmaceutical compositions containing the compounds.

DESCRIPTION OF THE FIGURES

FIG. 1 A shows the comparison of Compound 1 to the placebo and Apoquel.

FIG. 1 B shows the effect of three different doses of Compound 1.

DETAILED DESCRIPTION OF THE INVENTION

Figure 1A:
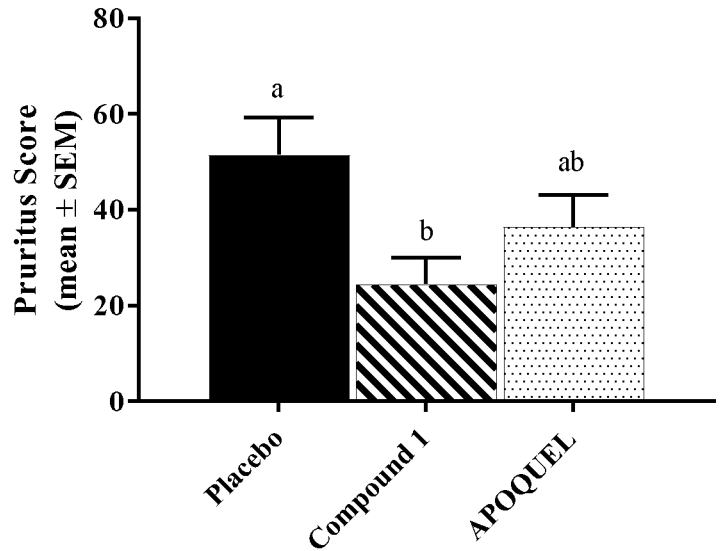
FIG. 1 displays the results of Compound 1 when tested in the IL-31 Induced Itching Model.

The present invention provides compounds of formula I or pharmaceutically acceptable salts or stereoisomers thereof:

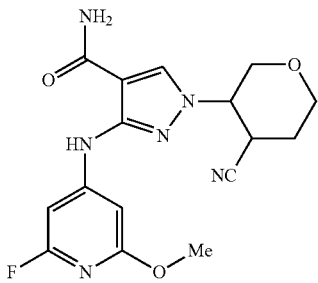

I

In an embodiment, the compound of Formula I is

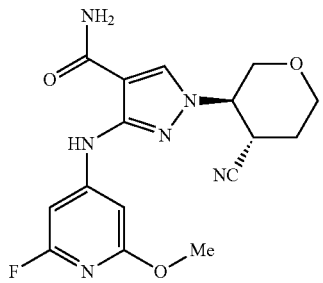 [SMILES: COc1cc(Nc2nn([C@H]3COCC[C@@H]3C#N)cc2C(N)=O)cc(F)n1]

In one embodiment, the compounds of the instant invention are selective JAK1 inhibitors relative to JAK2 and JAK3. In an embodiment, the compounds of the instant invention are selective JAK1 inhibitors relative to JAK2 or JAK3. The determination of relative selectivity for a given compound of JAK1 inhibition is defined as the relative ratio of the (JAK2 $IC_{50}$ value/JAK1 $IC_{50}$ value) is at least 2. Also, the relative ratio of the (JAK3 $IC_{50}$ value/JAK1 $IC_{50}$ value) is at least 500.

In yet another embodiment, for a given compound, the relative ratios of the (JAK2 $IC_{50}$ value/JAK1 $IC_{50}$ value) is at least 5 or is at least 10. In another embodiment, the relative ratio of the (JAK3 $IC_{50}$ value/JAK1 $IC_{50}$ value) is at least 500 or is at least 750 or is at least 1000.

Another embodiment of the invention is a pharmaceutical composition comprising a compound of Formula I or a pharmaceutically acceptable salt, or a stereoisomer thereof and a pharmaceutically acceptable carrier.

Another embodiment is a method for the treatment of a JAK-1 mediated disease comprising administering to a mammal in need thereof a therapeutically effective amount of a compound of Formula I or a pharmaceutically acceptable salt thereof or a pharmaceutical composition comprising a compound of Formula I.

A further embodiment is a method of treatment wherein the JAK-1 mediated disease is one that can be ameliorated by the selective inhibition of a Janus kinase JAK1 relative to JAK 2 and JAK 3.

In another embodiment, the disease is selected from allergic dermatitis, atopic dermatitis, arthritis, keratoconjunctivitis sicca, autoimmune diseases or disorders and cancer.

In another embodiment, the disease is atopic dermatitis.

In an embodiment, the disease is an autoimmune disease or disorder.

In an embodiment, the disease is arthritis.

In another embodiment, the mammal is a companion animal mammal.

In another embodiment, the companion animal is a dog, a cat, or a horse.

In an embodiment, the disease is keratoconjuncivitis sicca.

In a further embodiment, the administration is orally, parenterally or topically.

In another embodiment, the selective inhibition is of Janus kinase JAK1 relative to JAK 2.

In another embodiment, the selective inhibition is of Janus kinase JAK1 relative to JAK 3.

In a further embodiment, the ratio of JAK2($IC_{50}$)/JAK1 ($IC_{50}$) is a least 5, at least 10, at least 12.

In another embodiment, the ratio of JAK3($IC_{50}$)/JAK1 ($IC_{50}$) is a least 1000 or at least 750 or at least 500.

In another embodiment, the daily dose of the compound is from about 0.001 mg/kg to about 100 mg/kg or about 0.01 mg/kg to about 10 mg/kg or about 0.1 mg/kg to about 3.0 mg/kg or about 0.2 mg/kg to about 1.0 mg/kg body weight.

Evidence Supporting JAK1 Inhibition and Selectivity

Results from clinical trials with multi JAK inhibitors Tofacitinib (JAK1/JAK2/JAK3) (Kremer et al., Arthritis and Rheumatism 2009 "The safety and efficacy of a JAK inhibitor in patients with active RA", Fleishman et al, Arthritis and Rheumatism 2010 "Tofacitinib in patients with active RA", Fleishman et al, NEJM 2012 "Placebo controlled trial of Tofacitinib monotherapy in RA") and Baricitinib (JAK1/JAK2) (Greenwald et al, ACR annual meeting November 2010 "A randomized dose-ranmging, PBO-controlled study of TNCB028050, a selective JAK1 and JAK2 inhibitor, in subjects with active RA") support the hypothesis that high levels of efficacy can be achieved through targeting JAK inhibition. However, dose limiting adverse events have limited the efficacy and use of these agents. Significant hematopoetic AEs, specifically anemia, were observed in patients taking both Tofacitinib and Baricitinib, with a greater incidence and severity at higher doses. This is anticipated to be due to inhibition of EPO signaling, a growth factor critical for red blood cell development that signals via JAK2. Inhibition of EPO also leads to an inability to recover from anemia of chronic disease. Approximately 40% of RA patients suffer from anemia of chronic disease (Masson. Joint Bone Spine 2011 "Rheumatopid Anemia", Han et al, *J Rheumatology* 2007 "Association of anemia and physical disability among patients with RA"). The current treatment paradigm is to treat the inflammation that causes this anemia, however treatment with multi-JAK inhibitors that also inhibit EPO signaling cancel out the benefits on hemoglobin levels from treating the inflammation. Specific JAK1 inhibitors would not impact EPO signaling, would not be limited by anemia AEs, and would allow hemoglobin levels to rebound after inflammation was reversed.

Additional clinical evidence supporting the JAK1 hypothesis comes from Tocilizumab, an antibody targeting the IL-6 receptor (IL-6 signals through JAK1 and JAK2). High levels of efficacy are achieved with this biologic agent without inducing anemia, and anemia of inflammation is successfully reversed (Emery et al, Ann Rheum Dis 2008 "IL-6 receptor inhibition with tocilizumab improves treatment outcomes in patients with RA refractory to anti-TNF biologicals: results of a 24-week multicenter randomized placebo-controlled trial", Mashizume et al, Rheumatol Int. 2010 "Tocilizumab, a humanized anti-IL-6 receptor antibody, improved anemia in monkey arthritis by suppressing IL-6 induced hepcidin production").

"Patient" as used herein refers to a mammal that has been the object of treatment, observation, or experiment.

"Mammal" means mammalian animals. The mammal may be male or female. The mammal may be one or more selected from the group consisting of humans, bovine (e.g., cows), porcine (e.g., pigs), ovine (e.g., sheep), capra (e.g., goats), equine (e.g., horses), canine (e.g., domestic dogs), feline (e.g., house cats), Lagomorpha (rabbits), rodents (e.g., rats or mice), *Procyon lotor* (e.g., raccoons). In particular embodiments, the mammal is a companion animal (e.g. canine, feline or equine).

"Therapeutically effective amount" means that amount of a drug or pharmaceutical agent that will elicit the biological or medical response of a tissue, a system, animal or human that is being sought by a researcher, veterinarian, medical doctor or other clinician.

The term "treatment" or "treating" includes alleviating, ameliorating, relieving or otherwise reducing the signs and symptoms associated with a disease or disorder.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of formula I, and pharmaceutically acceptable excipients.

Optical Isomers-Diastereomers-Geometric Isomers-Tautomers

Compounds of formula I contain one or more asymmetric centers and can thus occur as racemates and racemic mixtures, single enantiomers, diastereomeric mixtures and individual diastereomers. The present invention is meant to comprehend all such isomeric forms of the compounds of formula I, either as single species or mixtures thereof.

Some of the compounds described herein contain olefinic double bonds, and unless specified otherwise, are meant to include both E and Z geometric isomers.

Specific embodiments of the present invention include a compound which is selected from the group consisting of the subject compounds of the Examples herein or a pharmaceutically acceptable salt thereof.

The compounds of the present invention may contain one or more asymmetric centers and can thus occur as "stereoisomers" including racemates and racemic mixtures, enantiomeric mixtures, single enantiomers, diastereomeric mixtures and individual diastereomers. Each such asymmetric center will independently produce two optical isomers and it is intended that all of the possible optical isomers and diastereomers in mixtures and as pure or partially purified compounds are included within the scope of this invention. The present invention is meant to comprehend all such isomeric forms of these compounds. When bonds to the chiral carbon are depicted as straight lines in the Formulas of the invention, it is understood that both the (R) and (S) configurations of the chiral carbon, and hence both enantiomers and mixtures thereof, are embraced within the Formula. For example, Formula I shows the structure of the class of compounds without specific stereochemistry. When the compounds of the present invention contain one chiral center, the term "stereoisomer" includes both enantiomers and mixtures of enantiomers, such as the specific 50:50 mixture referred to as racemic mixtures.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Enantiomers can also be separated by use of chiral HPLC column.

The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Salts

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzyl ethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like.

It will be understood that, unless otherwise specified, references to the compound of formula I, as well as specific compounds are meant to also include the pharmaceutically acceptable salts.

Furthermore, some of the crystalline forms for compounds of the present invention may exist as polymorphs and as such all forms are intended to be included in the present invention. In addition, some of the compounds of the instant invention may form solvates with water (hydrates) or common organic solvents. Such solvates are encompassed within the scope of this invention.

Labelled Compounds

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium (1H) and deuterium (2H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Utilities

Compound of formula I or its pharmaceutically acceptable salts and pharmaceutical compositions can be used to treat or prevent a variety of conditions or diseases mediated by Janus kinases, in particular diseases or conditions that can be ameliorated by the inhibition of a Janus kinase such as JAK1, JAK2 or JAK3. Such conditions and diseases include, but are not limited to:

(1) arthritis, including rheumatoid arthritis, juvenile arthritis, and psoriatic arthritis; (2) asthma and other obstructive airways diseases, including chronic asthma, late asthma, airway hyper-responsiveness, bronchitis, bronchial asthma, allergic asthma, intrinsic asthma, extrinsic asthma, dust asthma, recurrent airway obstruction, and chronic obstruction pulmonary disease including emphysema; (3) autoimmune diseases or disorders, including those designated as single organ or single cell-type autoimmune disorders, for example autoimmune thyroiditis, autoimmune hemolytic anemia, autoimmune atrophic gastritis of pernicious anemia, autoimmune encephalomyelitis, autoimmune orchitis, autoimmune thrombocytopenia, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, rheumatoid arthritis, Sjogren-like syndrome, polymyositis-dermatomyositis, systemic sclerosis, polyarteritis nodosa, and pemphigus, and additional autoimmune diseases, which can be B-cell (humoral) based or T-cell based, including ankylosing spondylitis, Wegener's granulomatosis, autoimmune alopecia, Type I or juvenile onset diabetes, and thyroiditis; (4) cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma, leukemia, including acute myelogenous leukemia and chronic myelogenous leukemia, kidney cancer, lung cancer, muscle cancer, bone cancer, bladder cancer, brain cancer, melanoma including oral and metastatic melanoma, Kaposi's sarcoma, myelomas including multiple myeloma, myeloproliferative disorders, proliferative diabetic retinopathy, and angiogenic-associated disorders including solid tumors; (5) diabetes, including Type I diabetes and complications from diabetes; (6) eye diseases, disorders or conditions including autoimmune diseases of the eye, keratoconjunctivitis, vernal conjunctivitis, uveitis and lens-induced uveitis, keratitis, herpetic keratitis, conical keratitis, corneal epithelial dystrophy, keratoleukoma, ocular premphigus, scleritis, Vogt-Koyanagi-Harada-like syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization; (7) intestinal inflammations, allergies or conditions including Crohn's disease and/or ulcerative colitis, inflammatory bowel disease, coeliac diseases, proctitis, eosinophilic gastroenteritis, and mastocytosis; (8) neurodegenerative diseases including motor neuron disease, cognitive dysfunction syndrome, Parkinson's disease, amyotrophic lateral sclerosis, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia, and platelet aggregation; (9) skin diseases, conditions or disorders including atopic dermatitis, eczema, psoriasis, scleroderma, pruritus and other pruritic conditions; (10) allergic reactions including anaphylaxis, allergic rhinitis, allergic dermatitis, allergic urticaria, angioedema, allergic asthma, or allergic reaction to insect bites, food, drugs, or pollen; (11) transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, and xeno transplantation.

Accordingly, another aspect of the present invention provides a method for the treatment or prevention of a JAK-mediated disease or disorder comprising administering to a mammal in need thereof a therapeutically effective amount of a compound of formula I. In one embodiment such diseases include asthma and rheumatoid arthritis. In another embodiment the disease is atopic dermatitis.

Another aspect of the present invention provides for the use of a compound of formula I in the manufacture of a medicament for the treatment or prevention of a JAK-mediated diseases or disorder.

Dose Ranges

The magnitude of prophylactic or therapeutic dose of a compound of formula I will, of course, vary with the nature and the severity of the condition to be treated and with the particular compound of formula I and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. In another embodiment, the daily dose is from about 0.2 mg per kg to about 1.0 mg/kg of body weight of a mammal. In another embodiment, the daily dose is from about 0.1 mg per kg to about 3.0 mg/kg of body weight of a mammal. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration may contain from 0.05 mg to 5 g of active agent compounded with an appropriate and convenient amount of carrier material which may vary from about 5 to about 99.95 percent of the total composition. Dosage unit forms will generally contain between from about 0.1 mg to about 0.4 g of an active ingredient, typically 0.5 mg, 1 mg, 2 mg, 5 mg, 10 mg, 25 mg, 50 mg, 100 mg, 200 mg, or 400 mg.

Pharmaceutical Compositions

Another aspect of the present invention provides pharmaceutical compositions comprising a compound of formula I with a pharmaceutically acceptable carrier.

Physiologically acceptable formulation carriers and excipients are known in the art and are described for example in "Gennaro, Remington: The Science and Practice of Pharmacy" ($20^{th}$ Edition, 2000). All such ingredients, carriers and excipients must be substantially pharmaceutically or veterinary pure and non-toxic in the amounts employed and must be compatible with the pharmaceutically active ingredients (i.e. the compound of Formula I). For the treatment of any of the diseases compounds, formula I may be administered orally, by inhalation spray, topically, parenterally or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example hepta-decaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of formula I may also be administered in the form of suppositories for rectal administration of the drug.

For topical use, creams, ointments, gels, solutions or suspensions, etc., containing the compound of formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

In an alternative embodiment, the compositions of the subject invention may be forumulated for ophthalmic administration.

Combinations with Other Drugs

For the treatment and prevention of JAK mediated diseases, compound of formula I may be co-administered with other therapeutic agents. Thus in another aspect the present invention provides pharmaceutical compositions for treating JAK mediated diseases comprising a therapeutically effective amount of a compound of formula I and one or more other therapeutic agents. In particular, for the treatment of the inflammatory diseases rheumatoid arthritis, psoriasis, inflammatory bowel disease, COPD, asthma and allergic rhinitis a compound of formula I may be combined with agents such as: (1) TNF-α inhibitors such as Remicade® and Enbrel®); (2) non-selective COX-I/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including low dose methotrexate, lefunomide, ciclesonide, hydroxychloroquine, d-penicillamine, auranofin or parenteral or oral gold; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast; (8) antihistaminic H1 receptor antagonists such as cetirizine, loratadine, desloratadine, fexofenadine, astemizole, azelastine, and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclindinium bromide, glycopyrrolate, pirenzepine, and telenzepine; (11) β-adrenoceptor agonists such as metaproterenol, isoproterenol, isoprenaline, albuterol, salbutamol, formoterol, salmeterol, terbutaline, orciprenaline, bitolterol mesylate, and pirbuterol, or methylxanthanines including theophylline and aminophylline, sodium cromoglycate; (12) insulin-like growth factor type I (IGF-1) mimetic; (13) inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate.

Methods of Synthesis

Schemes and Examples

The abbreviations used herein have the following tabulated meanings. Abbreviations not tabulated below have their meanings as commonly used unless specifically stated otherwise.

| | |
|---|---|
| ACN | Acetonitrile |
| Chiral SFC | chiral super critical fluid chromatography |
| DBU | 1,8-diazabicyclo[5.4.0]undec-7-ene |
| DCM | Dichloromethane |
| DMSO | dimethyl sulfoxide |
| DTT | Threo-1,4-dimercapto-2,3-butanediol (Cleland's reagent) |
| EtOAc | ethyl acetate |
| GST | Glutathione S-transferase |
| HEPES | 4-(2-Hydroxyethyl)piperazine-1-ethane sulfonic acid, N-(2-Hydroxyethyl) piperazine-N'-) (2-ethanesulfonic acid |
| HTRF | Homogeneous Time Resolved Fluorescence |
| HPLC | high pressure liquid chromatography |
| LCMS | liquid chromatography mass spectrometry |
| MPLC | medium pressure liquid chromatography |
| $Na_2SO_4$ | sodium sulfate |
| NaOMe | sodium methoxide |
| $Pd_2(dba)_3$ | tris(dibenzylideneacetone)dipalladium(0) |
| $POCl_3$ | phosphorus (V) oxychloride |
| t-BuOH | tert-butanol |
| THF | Tetrahydrofuran |
| X-Phos | 2-dicyclohexylphosphino-2',4',6'-triisopropylbiphenyl |
| $Me_4$-Bu-X-Phos | di-tert-butyl[3,4,5,6-tetramethyl-2',4',6'-tri(propan-2-yl)biphenyl-2-yl]phosphane |
| NMR | nuclear magnetic resonance |
| TLC | thin layer chromatography |
| TMS | Trim ethyl silane |
| TRF | Time Resolved Fluorescence |

Alkyl Group Abbreviations

| | |
|---|---|
| Me | Methyl |
| Et | Ethyl |
| n-Pr | normal propyl |
| i-Pr | Isopropyl |
| n-Bu | normal butyl |
| i-Bu | Isobutyl |
| s-Bu | secondary butyl |
| t-Bu | tertiary butyl |
| c-Pr | Cyclopropyl |
| c-Bu | Cyclobutyl |
| c-Pen | Cyclopentyl |
| c-Hex | Cyclohexyl |

Methods of Synthesis

The compounds of the present invention can be prepared according to the following general schemes using appropriate materials, and are further exemplified by the subsequent specific examples. The compounds illustrated in the examples are not to be construed as forming the only genus that is considered as the invention. The illustrative Examples below, therefore, are not limited by the compounds listed or

13 by any particular substituents employed for illustrative purposes. Substituent numbering as shown in the schemes does not necessarily correlate to that used in the claims and often, for clarity, a single substituent is shown attached to the compound where multiple substituents are allowed under the definitions of the instant invention herein above.

Those skilled in the art will readily understand that known variations of the conditions and processes of the following preparative procedures can be used to prepare these compounds. The invention will now be illustrated in the following non-limiting Examples in which, unless otherwise stated:

All reactions were stirred (mechanically, stir bar/stir plate, or shaken) and conducted under an inert atmosphere of nitrogen or argon unless specifically stated otherwise.

All temperatures are degrees Celsius (° C.) unless otherwise noted.

Ambient temperature is 15-25° C.

Most compounds were purified by reverse-phase preparative HPLC, MPLC on silica gel, recrystallization and/or swish (suspension in a solvent followed by filtration of the solid).

The course of the reactions was followed by thin layer chromatography (TLC) and/or LCMS and/or NMR and reaction times are given for illustration only.

All end products were analyzed by NMR and LCMS.

Intermediates were analyzed by NMR and/or TLC and/or LCMS.

Method 1

Commercially Available/Previously Described Materials

The following table lists commercial sources, and previously disclosed synthetic routes for chemical materials employed in the synthesis of intermediates, and Examples of the instant invention. The list is not intended to be exhaustive, exclusive, or limiting in any way.

| Structure | IUPAC Name | Vendor |
|---|---|---|
| 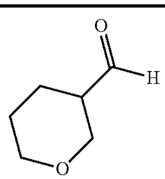 | tetrahydro-2H-pyran-3-carbaldehyde | J&W Pharmlab LLC |
| 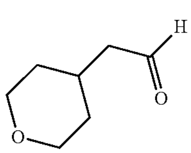 | tetrahydro-2H-pyran-4-ylacetaldehyde | Maybridge |

Intermediates

The following experimental procedures detail the preparation of chemical materials used in the synthesis of Examples of the instant invention. The exemplified procedures are for illustrative purposes only, and are not intended to limit the scope of the instant invention in any way.

14

Synthesis Scheme

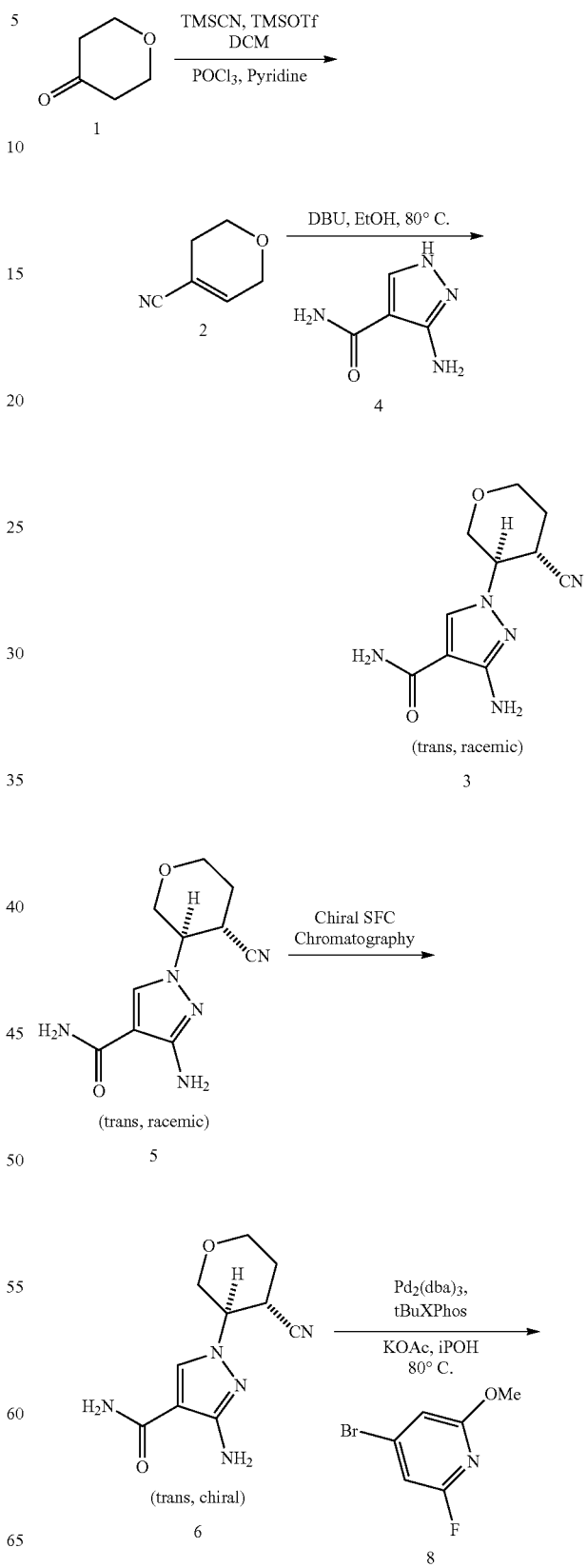

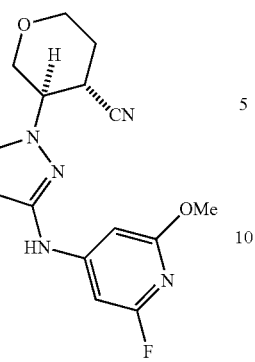

7

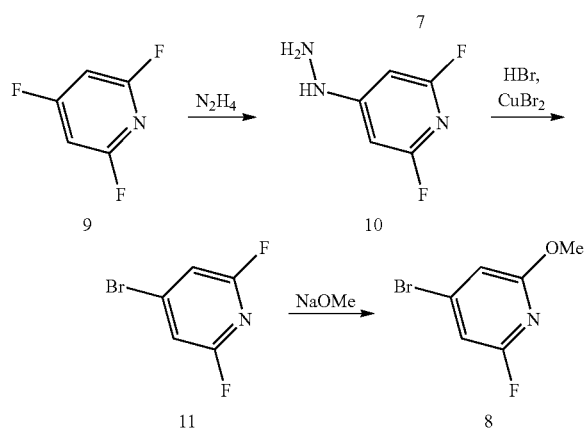

Intermediate 2:
3,6-Dihydro-2H-pyran-4-carbonitrile

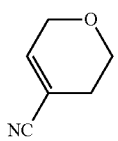

To a solution of trimethylsilyl cyanide (28.0 g, 288 mmol) in dichloromethane (100 mL) were sequentially added tetrahydro-4H-pyran-4-one 1 (24 g, 243 mmol) and trimethylsilyl triflate (1.6 g, 7.2 mmol) at 0° C. The resulting solution was stirred at 0° C. for 1 hour before the addition of pyridine (300 mL) and phosphoryl chloride (110 g, 719 mmol). The mixture was refluxed for 12 hours, and then poured into a mixture of 2 N aqueous hydrochloric acid solution (600 mL), crushed ice (180 mL) and ether (600 mL) at 0° C. The mixture was vigorously stirred for 15 minutes, and then extracted with ether (3×1 mL). All the organic solution was washed with brine (2×300 mL), dried over anhydrous sodium sulfate, filtered and concentrated in vacuo. The crude residue was purified by flash column chromatography with 1-2% ethyl acetate in hexane to afford the title compound as a yellow oil. $^1$H NMR (300 MHz, CDCl$_3$) δ 6.62-6.59 (m, 1H), 4.29-4.21 (m, 2H), 3.78 (t, J=5.4 Hz, 2H), 2.34-2.30 (m, 2H).

Intermediate 5: 3-Amino-1-((3R,4S) or (3S,4R)-4-cyano-tetrahydro-2H-pyran-3-yl)-1H-pyrazole-4-carboxamide

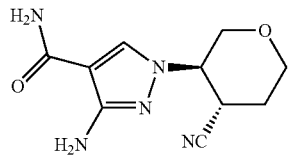 [SMILES: N#C[C@H]1CCOC[C@@H]1n1cc(C(N)=O)c(N)n1]

A mixture of 3-amino-1H-pyrazole-4-carboxamide 4 (804 g, 4.59 mol), 3,6-dihydro-2H-pyran-4-carbonitrile 2 (1000 g, 9.17 mol) and DBU (2435 g, 16 mol) in ethanol (800 mL) was stirred at 70° C. overnight under nitrogen, and then concentrated in vacuo. The crude residue was purified by silica gel flash column chromatography with 2-5% methanol in dichloromethane to afford the a racemic mixture of title compound and its enantiomer as a yellow solid (269 g, 25% yield).

Chiral separation: 380 g of the racemic compound was dissolved in ACN/MeOH (1:1) to a concentration of 25 mg/mL. Injections of 16 mL were made on a Thar 350 preparative SFC (Column: ChiralPak IC-10 μM, 300×50 mm; Mobile phase: 45% 2-propanol, 55% CO2; Flow rate: 220 mL/min; Column temperature: 38° C.). After separation, the fractions were dried by rotary evaporation. The second (slower eluting) peak was used to prepare the following compounds.

$^1$H NMR (500 MHz, DMSO-d$_6$) δ 8.03 (s, 1H), 7.36 (brs, 1H), 6.80 (brs, 1H), 5.36 (s, 2H), 4.86-4.31 (td, J=10.5, 4.5 Hz, 1H), 3.91-3.88 (dd, J=11.5, 4.5 Hz 1H), 3.86-3.83 (m, 1H), 3.53-3.50 (m, 2H), 3.39-3.33 (td, J=11.5, 2 Hz, 1H), 2.10-2.07 (m, 1H), 1.95-1.87 (m, 1H). LRMS (ESI) calc'd for C$_{10}$H$_{14}$N$_5$O$_2$ [M+H]$^+$: 236, Found: 236.

Intermediate 10: 2,6-difluoro-4-hydrazinylpyridine

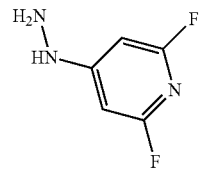

To an oven dried round bottom flask with magnetic stir bar under an atmosphere of N2 2,4,6-trifluoropyridine 9 (7 g, 52.6 mmol, 1 equiv), THF (52.6 mL, 1 M), and hydrazine (5.1 mL, 105 mmol, 2 equiv) were added. The reaction mixture was heated to 50° C. for 2 h, and then cooled to room temperature. The crude material was triturated with water (2×25 mL) and hexanes (25 mL), and then dried in vacuo overnight. The resulting solid was recrystallized in EtOAc to yield 2,6-difluoro-4-hydrazinylpyridine 10 (4.5 g, 31 mmol). $^1$H NMR (500 MHz, DMSO-d$_6$) δ 8.42 (s, 1H), 6.16 (brs, 2H), 4.46 (s, 2H).

Intermediate 11: 4-bromo-2,6-difluoropyridine

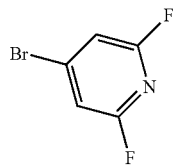

To an oven dried round bottom flask with magnetic stir bar under an atmosphere of N2 2,6-difluoro-4-hydrazinylpyridine 10 (13.24 g, 91 mmol), and chloroform (97 mL, 0.78 M) were added followed by dropwise addition (via addition funnel) of bromine (9.40 mL, 182 mmol, 2 equiv) at room temperature. The reaction mixture was heated to reflux for 6 h, and then cooled to room temperature and filtered through celite. The filtrate was washed with sat. aq. Na$_2$CO$_3$ (25 mL), brine (25 mL), dried over Na$_2$SO$_4$, and then filtered through celite and concentrated in vacuo. The crude 4-bromo-2,6-difluoropyridine 11 (11.8 g, 60.8 mmol) was used with out further purification. $^1$H NMR (500 MHz, CDCl$_3$) δ 7.04 (s, 2H).

Intermediate 8:
4-bromo-2-fluoro-6-methoxypyridine

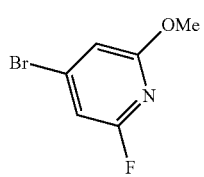

To an oven dried round bottom flask with magnetic stir bar under an atmosphere of N$_2$ 4-bromo-2,6-difluoropyridine 11 (10.8 g, 55.7 mmol), and methanol (111 mL, 0.5 M) were added followed by sodium methoxide (10.83 g, 50.1 mmol, 0.9 equiv) at room temperature. The reaction mixture was heated to 40° C. for 1 h, and then cooled to room temperature. The suspension was partituioned between EtAOc (100 mL) and water (50 mL). The organics were washed with brine (25 mL), dried over Na$_2$SO$_4$, filtered through celite, and concentrated in vacuo. The crude residue was purified using column chromatography (0-100% EtOAc in hexanes, gradient) to yield 4-bromo-2-fluoro-6-methoxypyridine 8 (7.29 g, 35.4 mmol). $^1$H NMR (500 MHz, CDCl$_3$) δ 7.77 (s, 1H), 7.63 (s, 1H), 3.86 (2, 3H).

Example 1: 1-((3R,4S) or (3S,4R)-4-cyanotetrahydro-2H-pyran-3-yl)-3-((2-fluoro-6-methoxypyridin-4-yl)amino)-1H-pyrazole-4-carboxamide

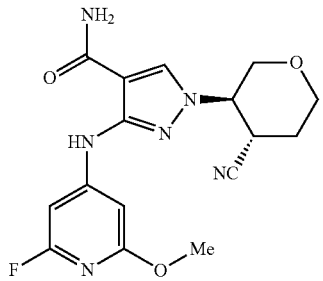 [SMILES: COc1cc(Nc2nn([C@H]3COCC[C@@H]3C#N)cc2C(N)=O)cc(F)n1]

A 500 mL 3-neck flask was fitted with a reflux condenser and J-KEM thermocouple, then charged with 3-amino-1-((3R,4S)-4-cyanotetrahydro-2H-pyran-3-yl)-1H-pyrazole-4-carboxamide 5 (10.0 g, 42.5 mmol), 4-bromo-2-fluoro-6-methoxypyridine 8 (14.1 g, 63.7 mmol), potassium acetate (6.26 g, 63.8 mmol) and 2-propanol (150 ml). The reactions mixture was sparged with dinitrogen gas for 20 min, then Pd$_2$(dba)$_3$ (1.95 g, 2.13 mmol) and 2-di-tert-butylphosphino-2',4',6'-triisopropylbiphenyl (2.00 g, 4.71 mmol) were added. The reaction mixture was then heated to 80° C. for 16.5 h. After cooling to 23° C., acetone (150 mL) was added and the mixture was stirred for 10 min, then filtered through celite with acetone elution. The filtrate was concentrated onto silica gel in vacuo and purified via flash-column chromatography (ISCO 220 g cartridge, gradient elution with 3-6% methanol-dicholoromethane). The product-containing fractions were concentrated to afford 1-((3R,4S) or (3S,4R)-4-cyanotetrahydro-2H-pyran-3-yl)-3-((2-fluoro-6-methoxypyridin-4-yl)amino)-1H-pyrazole-4-carboxamide as a bright yellow solid.
$^1$H NMR (600 MHz, DMSO-d6): δ 9.63 (s, 1H), 8.34 (s, 1H), 7.29 (s, 1H), 7.28 (s, 1H), 6.66 (d, 2H), 4.59 (m, 1H), 4.00 (m, 1H), 3.87 (m, 1H), 3.76 (s, 3H), 3.65-3.58 (m, 2H), 3.46 (m, 1H), 2.12 (m, 1H), 1.94 (m, 1H). LRMS (ESI) calc'd for C$_{16}$H$_{17}$FN$_6$O$_3$[M+H]$^+$: 361, Found: 361.

Biological Assays

Experimental Procedures

Jak Biochemical HTRF Enzyme Assay Protocol

The ability of compounds to inhibit the catalytic activity of JAK1, JAK2, JAK3, and TYK2 was quantified using a recombinant purified GST-tagged catalytic domain for each enzyme (InVitrogen/Life Technologies/ThermoFisher, catalogue #s: JAK1, #M4290; JAK2, #M4290; JAK3, #M4290; TYK2 #M4290) in an HTRF format biochemical assay. The reactions employed a common peptide substrate, LCB-EQEDEPEGDYFEWLW-NH2 (Merck). The basic assay protocol is as follows: First, 50 nL of diluted compounds in DMSO were dispensed into the wells of a dry 384-well assay plate (Perkin Elmer Opti-plate, catalogue #6007290) using a Labcyte Echo 555 acoustic dispenser. Subsequent reagent additions employed an Agilent Bravo automated liquid handler. Next, 18 µL of 1.11× enzyme, added at the lowest concentration possible to obtain a 10 fold above background control that kept the reaction at initial velocity during the course of the reaction (see table below) and 1.11× substrate in 1× assay buffer (Invitrogen kinase buffer #PV3189, 2 mM DTT, 0.05% BSA) were added to the wells, shaken and then incubated for 30 minutes at room temperature to allow compound binding and reach equilibrium. After this step, 2 µL of 10×ATP in 1× assay buffer was added to initiate the kinase reaction, keeping the concentration of ATP at a concentration equal to the apparent Km calculated for each enzyme preparation (see table below) and the plates were shaken and then incubated at 23° C. for 80 minutes. At the end of the incubation, 20 µL of 2× stop buffer (streptavidin-Dylight 650 (ThermoFisher #84547B/100 mL), Europium-tagged pY20 antibody (Perkin Elmer #AD0067), EDTA, HEPES, and Triton) was added to quench the reaction. Plates were shaken and centrifuged and then incubated 60 minutes at room temperature and then read on a Perkin Elmer Envision (λex=337 nm, λem=665 and 615 nm, TRF delay time=20 s). HTRF signal=10,000*665 nm reading/615 nm reading. After normalization to untreated controls, the percent inhibition of the HTRF signal at each compound concentration was calculated. The plot of percent inhibition versus the log value of compound concentration was done as described above for cell assays to calculate IC50 values. Final reaction conditions were:

| Enzyme | [E] (nM) | [peptide] (µM) | [ATP] (µM) | [Eu-pY20] (nM) | [SA-Dylight] (nM) |
|---|---|---|---|---|---|
| JAK1 | 1.0 | 0.75 | 30.1 | 9 | 312.5 |
| JAK2 | 0.0075 | 0.75 | 7.0 | 9 | 312.5 |
| JAK3 | 0.015 | 0.75 | 1.7 | 9 | 312.5 |
| Tyk2 | 2.0 | 0.75 | 9.3 | 9 | 312.5 |

Compound concentrations tested were 1496, 499, 175, 49.9, 18.7, 6.2, 2.1, 0.75, 0.24, 0.075, and 0.0125 nM. The final [DMSO] was adjusted 0.25%.

Assay Performance and Data Quality Control:

Performance of enzyme assays was tracked by calculating minimum significant ratio (MSR) values across assay runs for pan- and selective-JAK reference molecules:

biology/cellular-pathway-analysis/cellsensor-cell-lines.html), in two independent cell lines engineered to detect IL4, IL6 and EPO signaling. In brief, CellSensor® cell lines (see details below for each assay) carrying a stably integrated β-Lactamase reporter gene under control of specific cis-regulatory STAT elements responsive to the pathway being monitored were pre-treated with test compounds serially diluted in DMSO (see preparation and dosing of compounds and agonist cytokines section). Following incubation with compounds, IL6, or EPO were added to each cognate cell line at a concentration equal to a dose necessary to achieve 80% of the maximal response (EC80). After cytokine stimulation, cellular levels of 1-Lactamase activity were detected in situ using LiveBLAzer™ Loading Kit (LiveBLAzer™-FRET B/G substrate, CCF4-AM from Life Technologies), where fluorescence of the substrate (emitting fluorescence at 405 nm) and cleaved product (emitting fluorescence at 488 nm) were quantified in an Acumen Explorer ex3 reader (TTP Labtech). Normalized fluorescence values reporting percentage inhibition of test com-

| Reference Compound | Structure | Name | Source |
|---|---|---|---|
| A | 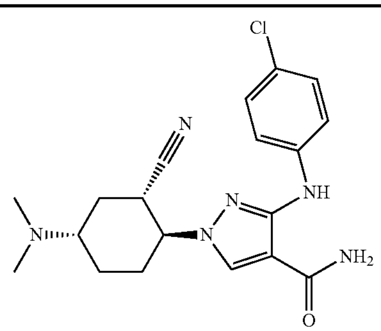 | 3-[(4-chlorophenyl)amino]-1-[(1S,2S,4S or 1R,2R,4R)-2-cyano-4-(dimethylamino)cyclohexyl]-1H-pyrazole-4-carboxamide | WO2013/040863, page 225, compound 28-117 |
| B | 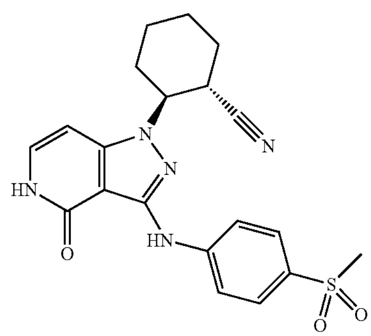 [SMILES: CS(=O)(=O)c1ccc(Nc2nn([C@H]3CCCC[C@@H]3C#N)c3cc[nH]c(=O)c23)cc1] | (1S,2S)-2-(3-{[4-(methylsulfonyl)phenyl]amino}-4-oxo-4,5-dihydro-1H-pyrazolo[4,3-c]pyridin-1-yl)cyclohexanecarbonitrile | WO2014/146490, page 163, compound 3-5 |

Potencies for Reference Compound No. 1, aJAK1 selective, were: JAK1 IC50=1.47 nM+/−0.40, N=392; JAK2 IC50=19.04+/−4.15 nM, N=393; JAK3 IC50=1351.45 nM+/−129.93, N=398 and TYK2 IC50=13.96 nM+/−3.17, N=394.

Potencies for Reference Compound No. 2, a JAK1 pan-inhibitor, were: JAK1 IC50=0.17 nM+/−0.06, N=399; JAK2 IC50=1.00+/−0.29 nM, N=400; JAK3 IC50=21.95 nM+/−6.08, N=404 and TYK2 IC50=0.28 nM+/−0.09, N=401.

Cell Pathway Engagement JAK Assays:

Inhibition of the activity of JAK1 and JAK2 kinases in intact cells was quantified in antagonist mode using CellSensor® transcriptional reporter technology (Life Technologies/ThermoFisher: https://www.thermofisher.com/us/en/home/industrial/pharma-biopharma/drug-discovery-development/target-and-lead-identification-and-validation/pathwaypounds treated wells were plotted against the Log value of the concentration of each of ten doses selected to build a dose response curve (DRC) using a 4-parameter fit dose response equation to calculate the concentration necessary to achieve 50% inhibition of the maximal activity (IC50, or potency value) in Assay Data Analyzer software (Merck Frosst Canada & Co—2003). Percentage inhibition was calculated as function of the levels of beta lactamase measured in DMSO control treated wells, 0% inhibition, vs. levels of 13-Lactamase in wells treated with a dose of a pan-JAK inhibitor sufficient to achieve 100% blockade of 1-Lactamase production. Incubation with compounds, cytokines and LiveBLAzer™ were carried out at 37° C. in a tissue culture incubator maintained at 90% humidity and 5% $CO_2$.

Agonist and cell line pairings used to quantify functional inhibition of JAK regulated pathways were as follows:

Interleukin 6 (IL6)—JAK1/JAK2-STAT4 Pathway:

CellSensor™ SIE-bla ME-180 cells carrying a stably integrated β-Lactamase reporter gene under control of the Sis-Inducible Element (SIE).

Erythropoietin (EPO)—JAK2-STAT5 Pathway:

CellSensor irf1-bla TF-1 cells carry a stably integrated β-Lactamase reporter gene under control of the STAT5 Response Elements present in the Interferon Regulatory Factor I (IRF1) gene promoter.

Preparation and Dosing of Compounds and Cytokines:

10 mM stock compound stock solutions prepared in DMSO were serially diluted 1:3 ten times, in DMSO using a Tecan Freedom EVO-2 200 automated liquid handler in Echo Qualified 384-Well Polypropylene Microplate (384PP), flat bottom, clear (Labcyte, Cat #P-05525). Sixty nL of each dose of compound were dispensed using an ECHO Acoustic Dispenser 550 (Labcyte) in a dry 384 Well Flat Clear Bottom Black Polystyrene TC-Treated Microplates (Corning Cat#3712). Each CellSensor® cell line was subsequently plated as per supplier's instructions (30,000 cells in 32 μL/well) and mixed with compound. Following a 60 minute incubation cells were subsequently stimulated by addition of 8 μL of cognate cytokine (EC80 dose of IL6 and EPO) and incubated for an additional 3 hours, before adding LiveBLAzer™-FRET B/G substrate. Final doses of compound tested were: 14977; 4992; 1664; 554; 184; 61.6; 20.5; 6.8; 2.3 and 0.76 nM. The final DMSO concentration was kept at 0.15%.

Assay Performance and Data Quality Control:

Three parameters were used to validate quality of each individual assay run and to ensure development of narrow structure activity relationship (SAR) which enabled discerning differences between compounds whose potency varied by as low 3-4 folds:

(A) To verify that stimulation with cytokine was within the acceptable +/−5% of the dose necessary to achieve 80% stimulation, EC80, a 16 points agonist dose reponse curve (DRC) was included in every plate and this DRC was used to back calculate the level of stimulation reached across the plate. Top doses of the DRCs were: 500 ng/mL for IL6 and 100 ng/mL for EPO.

(B) DRCs for two reference compounds were included in each assay plate containing a total of 32 compounds per plate:

Reference Compound No. A, a JAK1 selective molecule, twelve fold more potent in the IL6 CellSensor assay: IC50=51.9+/−23.6 nM, N=627 over the EPO CellSensor assay: IC50=623.5+/−132.3 nM, N=617. Activity in the IL4 CellSensor assay was: IC50=25.7+/−8.4 nM, N=307

Reference Compound No. B., a pan-JAK inhibitor, that exhibited potency within two-three fold across both assays. IL6/JAK1-JAK2 assay: IC50=21+/−9.1 nM, N=652 over and EPO/JAK2 assay: IC50=39.5+/−12.4 nM, N=626

(C) Assay reproducibility across replicate plates and independent runs was monitored by calculating minimal significant ratio (MSR, see Eastwood et al., Journal of Biomolecular Screening 11(X); 2006) tracking IC50 potency values for both reference compounds.

Biological Data

Examples of the instant invention were evaluated in JAK1, JAK2, and JAK3 in vitro binding assays, and IL-6 and EPO cell pathway engagement assays, as described above. Table 1 tabulates the IC50 values of the instant invention in the JAK1, JAK2, and JAK3 in the in vitro binding assays, and the IL-6 and EPO cell pathway engagement assays, as well as the ratio of the JAK2/JAK1 IC50s, JAK3/JAK1 IC50s, and the EPO/IL-6 IC50s. Table 2 tabulates the pharmacokinetic parameters of the instant invention in the dog after IV administration. Table 3 shows comparable data for other JAK1 compounds.

TABLE 1

| Compound | JAK1 IC50 (nM) | JAK2 IC50 (nM) | JAK3 IC50 (nM) | Ratio JAK2/1 | Ratio JAK3/1 | IL-6 IC50 (nM) | EPO IC50 (nM) | Ratio EPO/IL-6 |
|---|---|---|---|---|---|---|---|---|
| 1 | 0.43 | 5.89 | 1130 | 14 | 2628 | 41.8 | 459.7 | 11 |

TABLE 1-continued

| Compound | JAK1 IC50 (nM) | JAK2 IC50 (nM) | JAK3 IC50 (nM) | Ratio JAK2/1 | Ratio JAK3/1 | IL-6 IC50 (nM) | EPO IC50 (nM) | Ratio EPO/IL-6 |
|---|---|---|---|---|---|---|---|---|
| Enantiomer of 1 | 17.7 | 215.9 | >1249 | 12.2 | >70 | 2444.5 | 9484.8 | 3.9 |

TABLE 2

Dog Pharmacokinetics (PK) of Compound 1

| PK Parameter | Value |
|---|---|
| Dose (mg/kg I.V.) | 0.25 |
| AUC (μM.h) | 1.29 |
| CL (mL/min/kg) | 9.42 |
| Vdss (L/kg) | 1.95 |
| T1/2 (h) | 4.38 |

Comparative Examples

TABLE 3

| Compound | | JAK1 IC50 (nM) | JAK2 IC50 (nM) | JAK2/1 | IL-6 IP (nM) | EPO IP (nM) | EPO/IL-6 |
|---|---|---|---|---|---|---|---|
| Tofacitinib | Chiral | 1.35 | | 1x | 96 | | 0.7x |
| Baricitinib | | 0.47 | | 0.4x | 40 | | 0.43x |

TABLE 3-continued

| Compound | JAK1 IC50 (nM) | JAK2 IC50 (nM) | JAK2/1 | IL-6 IP (nM) | EPO IP (nM) | EPO/IL-6 |
|---|---|---|---|---|---|---|
| Oclacitinib | 3.4 | | 2.0x | 230 | | 2.4x |
| JAKAFI | 1 | | 0.7x | 40 | | 0.2x |
| INCB39110 | 0.3 | | 10x | 97 | | 5x |

TABLE 3-continued

| Compound | | JAK1 IC50 (nM) | JAK2 IC50 (nM) | JAK2/1 | IL-6 IP (nM) | EPO IP (nM) | EPO/IL-6 |
|---|---|---|---|---|---|---|---|
| GLPG0634 | 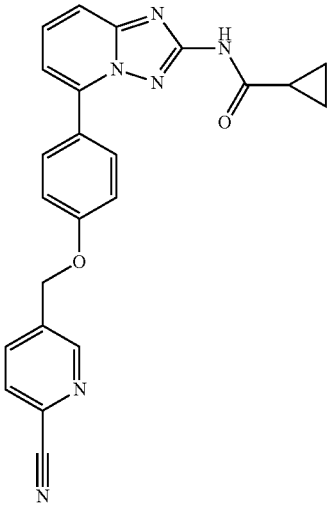 [SMILES: N#Cc1ccc(COc2ccc(-c3cccc4nc(NC(=O)C5CC5)nn34)cc2)cn1] | 0.63 | | 4.8x | 40 | | 5x |
| Reference Compound A | 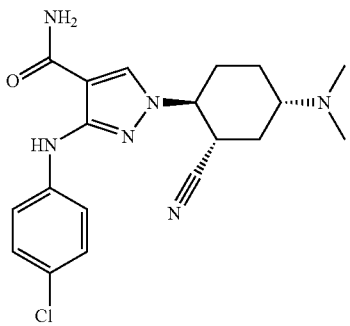 [SMILES: CN(C)[C@H]1CC[C@H](n2cc(C(N)=O)c(Nc3ccc(Cl)cc3)n2)[C@@H](C#N)C1] | 1.67 | | .11.4x | 57 | | 11x |

Safety Study for Compound 1.

A 6-week pilot target animal safety study was conducted for Compound 1. The drug was administered orally, as a compressed tablet, twice per day for 6 weeks to dogs at 1, 3, and 5 times the maximum exposure dose of 0.5 mg/kg, or once per day for 6 weeks to dogs at 5 times the maximum exposure dose of 1 mg/kg. No test article related effects were observed in clinical observations, fecal observations, body weight, body weight change, food consumption, physical examination parameters, blood pressure, ophthalmology, or cardiology. No test article related effects were observed in postmortem evaluations, including organ weights and macroscopic and microscopic findings. Based on the findings in this study, the no observed adverse effect level (NOAEL) is 5.0 mg/kg/day as a once a day dose or 2.5 mg/kg BID. The JAK-1 selectivity of Compound 1 was hypothesized to provide a greater margin of safety compared to a less selective compound such as oclacitinib (Apoquel®). These data from the pilot target animal safety study provide evidence for this hypothesis, and suggest that Compound 1 can effectively treat canine atopic dermatitis with an improved margin of safety.

Compound 1 in IL-31 Induced Itching Model

Figure 1B:
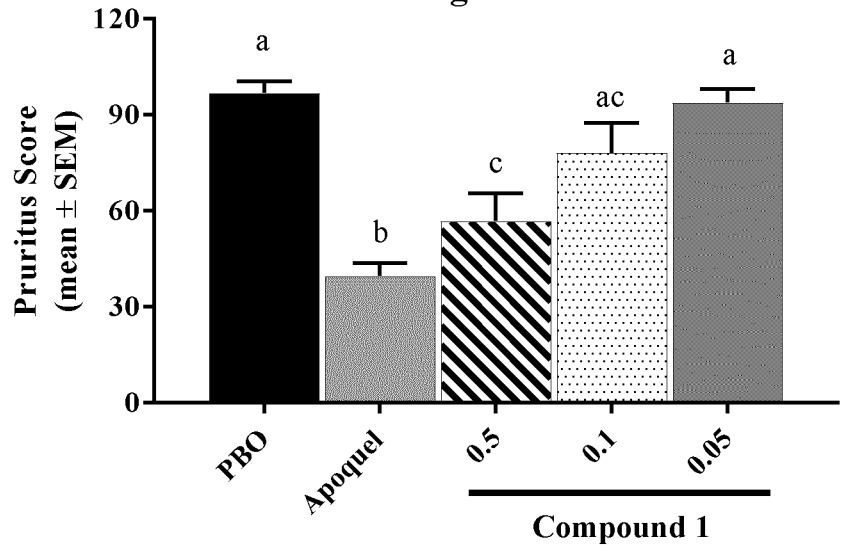

As a measure of JAK-1 inhibition in vivo, and by extension the anticipated clinical efficacy of Compound 1, we evaluated Compound 1 in a relevant pharmacodynamic model and included a clinical reference. Canine interlukin-31 (cIL-31) has been demonstrated to be involved in the pruritus associated with atopic and allergic dermatitis in dogs [Gonzales et al., *Vet Dermatol* 2013; 24: 48-e12], and IL-31 can activate JAK-1 and JAK-2 signaling molecules after binding to its receptor complex [Zhang et al., *Cytokine & Growth Factor Reviews* 19 (2008) 347-356]. cIL-31 administration to Beagle dogs produces a robust pruritic response that can be inhibited by prior treatment with the JAK inhibitor oclacitinib [Gonzales et al., *Vet Dermatol* 2016; 27: 34-e10]. Using a randomized, non-blinded, crossover study design, Compound 1 (1 mg/kg body weight), Apoquel®, or placebo was dosed to laboratory Beagle dogs 2 h prior to a cIL-31 challenge (approximate Tmax of Compound 1 and Apoquel®). Dogs were observed for 2 h after cIL-31 challenge, and the time animals were engaged in pruritic behaviors was recorded. In this study, Compound 1 significantly suppressed the cIL-31 induced pruritus; the magnitude was similar to Apoquel. In a second study using a randomized, non-blinded crossover design, several doses of Compound 1 were evaluated (0.5, 0.1 and 0.05 mg/kg body weight); Apoquel® and placebo treatments were also included. Compound 1 significantly suppressed pruritus at the 0.5 mg/kg body weight dose, but not at the 0.1 and 0.5 mg/kg body weight doses. The magnitude of effect was similar between 0.5 mg/kg Compound 1 and Apoquel®. See FIGS. 1A and 1B.

REFERENCES

Zhang Q., P. Putheti, Q. Zhou, Q. Liu, W. Gao. Structures and biological functions of IL-31 and IL-31 receptors. Cytokine & Growth Factor Reviews 19 (2008) 347-356.

Gonzales, A., W. R. Humphrey, J. E. Messamore, T. J. Fleck, G. J. Fici, J. A. Shelly, J. F. Teel, G. F. Bammert, S. A. Dunham, T E. Fuller and R. B. McCall. Interleukin-31: its role in canine pruritus and naturally occurring canine atopic dermatitis. Vet Dermatol 2013; 24: 48-e12.

Gonzales, A, T. J. Fleck, W. R. Humphrey, B. A. Galvan, M. M. Aleo, S. P. Mahabir, J.-K. Tena, K. G. Greenwood and R. B. McCall. IL-31-induced pruritus in dogs: a novel experimental model to evaluate nti-pruritic effects of canine therapeutics. Vet Dermatol 2016; 27: 34-e10.

Clinical assessment: The compound is being evaluated in a masked and randomized proof-of-concept study in dogs with a diagnosis of atopic dermatitis. The objective of this study is to evaluate the efficacy and tolerability of the compound against atopic dermatitis in client-owned dogs. The compound is administered at two doses and compared to a placebo control. Dogs are dosed orally twice daily for up to 14 days followed by once daily for up to 28 days, and are evaluated for pruritus and skin lesions using the Pruritus Visual Analog Scale (PVAS) and Canine Atopic Dermatitis Extent and Severity Index (CADESI-4) scoring tools, respectively.

The CADESI-4 is a severity scale used to grade skin lesions in clinical trials for treatment of dogs with atopic dermatitis (AD). Three lesion types (erythema, lichenification and alopecia/excoriation) are scored from 0 to 3 at each of 20 body sites, for a maximal score of 180, with proposed benchmarks for mild, moderate and severe AD skin lesions of 10, 35 and 60, respectively. The PVAS is a visual analog scale that contains features of both the severity of itching and behaviors associated with itching. It is commonly used to determine the severity of pruritus in clinical trials for treatment of dogs with AD.

CADESI-4: Thierry, O., Manolis, S., Nuttall, T., Bensignor, E., Griffin, C., Hill, P., for the International Committee on Allergic Diseases of Animals (ICADA). Validation of the Canine Atopic Dermatitis Extent and Severity Index (CADESI)-4, a simplified severity scale for assessing skin lesions of atopic dermatitis in dogs. Vet, Dermatol. 25:77-e25, 2014

PVAS: Hill, P. B., Lau, P., and Rybnicek, J. Development of an owner-assessed scale to measure the severity of pruritus in dogs. Vet. Dermatol. 18:301-308, 2007.

What is claimed is:

1. A compound of formula I or a pharmaceutically acceptable salt or stereoisomer thereof:

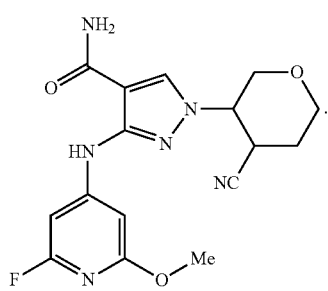

Formula I

2. The compound of claim 1, wherein the compound is

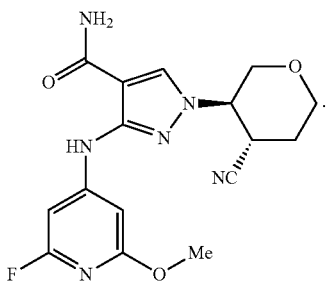 [SMILES: COc1cc(Nc2nn([C@H]3COCC[C@@H]3C#N)cc2C(N)=O)cc(F)n1]

3. A pharmaceutical composition comprising a compound of claim 2 or a pharmaceutically acceptable salt, or a stereoisomer thereof and a pharmaceutically acceptable carrier.

4. A method for the treatment of a JAK-1 mediated disease selected from the list consisting of allergic dermatitis, atopic dermatitis, arthritis, and keratoconjunctivitis sicca, comprising administering to a mammal in need thereof a therapeutically effective amount of the pharmaceutical composition of claim 3.

5. The method of claim 4 wherein the JAK-1 mediated disease in the mammal is one that can be ameliorated by the selective inhibition of a Janus kinase JAK1 relative to JAK 2 and JAK 3.

6. The method according to claim 4, wherein the disease is atopic dermatitis.

7. The method of claim 4, wherein the disease is arthritis.

8. The method of claim 5 wherein the mammal is a companion animal mammal.

9. The method of claim 8 wherein the companion animal is a dog, a cat, or a horse.

10. The method according to claim 4, wherein the disease is keratoconjuncivitis sicca.

11. The method of claim 5, wherein the administration is orally, parenterally or topically.

12. The method of claim 5, wherein the selective inhibition is of Janus kinase JAK1 relative to JAK 2.

13. The method of claim 5, wherein the selective inhibition is of Janus kinase JAK1 relative to JAK 3.

14. The method of claim 12, wherein the ratio of JAK2 ($IC_{50}$)/JAK1($IC_{50}$) is at least 5.

15. The method of claim 4, wherein the daily dose of the compound is from about 0.001 mg/kg to about 100 mg/kg.

16. The method of claim 13, wherein the ratio of JAK3 ($IC_{50}$)/JAK1($IC_{50}$) is at least 500.

17. A pharmaceutical composition comprising a compound of claim 1 or a pharmaceutically acceptable salt, or a stereoisomer thereof and a pharmaceutically acceptable carrier.

18. A method for the treatment of a JAK-1 mediated disease selected from the list consisting of allergic dermatitis, atopic dermatitis, arthritis, and keratoconjunctivitis sicca, comprising administering to a mammal in need thereof the pharmaceutical composition of claim 17.

* * * * *